United States Patent [19]

Kuiff et al.

[11] 4,135,078
[45] Jan. 16, 1979

[54] ELECTRICALLY HEATED WINDOW

[75] Inventors: Siegfried Kuiff; Heinz Ueberwolf, both of Herzogenrath, Germany

[73] Assignee: Saint-Gobain Industries, Neuilly-sur-Seine, France

[21] Appl. No.: 699,879

[22] Filed: Jun. 25, 1976

Related U.S. Application Data

[62] Division of Ser. No. 459,103, Apr. 8, 1974, Pat. No. 3,995,140.

[30] Foreign Application Priority Data

Apr. 12, 1973 [FR] France .................................. 73 13288
Mar. 8, 1974 [FR] France .................................. 74 07909

[51] Int. Cl.$^2$ .......................... H05B 3/26; H06B 7/12
[52] U.S. Cl. ............................ 219/203; 200/61.05; 219/522; 219/547; 338/35; 340/602
[58] Field of Search ............... 219/203, 522, 547, 509; 338/34, 35; 340/234, 235; 73/73; 200/61.05, 61.06, 61.04, 61.07; 318/DIG. 2, 483, 443; 15/250.12, 250.02

[56] References Cited

U.S. PATENT DOCUMENTS

| | | | |
|---|---|---|---|
| 2,407,215 | 9/1946 | Anderson | 15/250.02 |
| 3,555,289 | 1/1971 | Sobkow | 318/483 |
| 3,649,898 | 3/1972 | Inoue | 318/443 X |
| 3,794,847 | 2/1974 | Cadiou | 200/61.05 X |
| 3,832,527 | 8/1974 | Nagasima | 200/61.05 X |
| 3,934,111 | 1/1976 | Roselli et al. | 219/203 |
| 3,983,527 | 9/1976 | Ohsato et al. | 219/203 X |

*Primary Examiner*—Thomas J. Kozma
*Attorney, Agent, or Firm*—Pennie & Edmonds

[57] ABSTRACT

An electrically heated window for a vehicle includes a transparent sheet, a plurality of electrical resistance strips disposed on the sheet, and at least two closely spaced electrodes disposed on a surface of the sheet for detection of humidity on the surface of the sheet between them. The electrodes extend along the maximum slope of the window, and may extend downwardly unequal distances.

4 Claims, 8 Drawing Figures

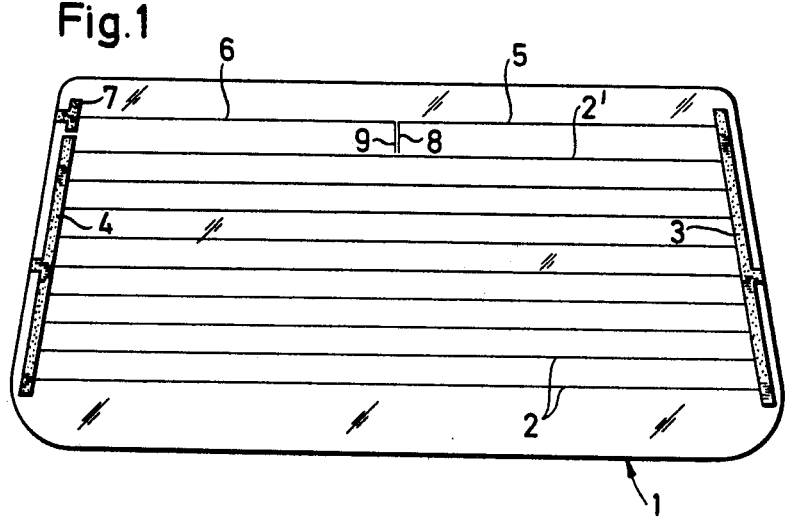
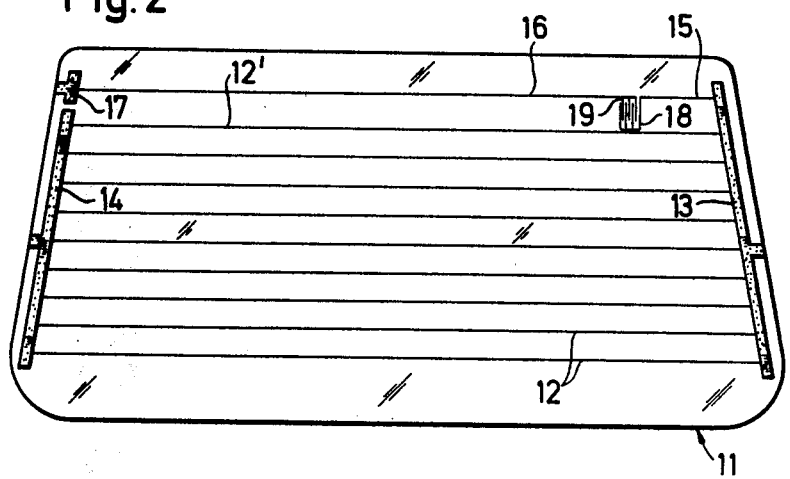

ELECTRICALLY HEATED WINDOW

This is a division, of application Ser. No. 459,103, filed Apr. 8, 1974, now U.S. Pat. No. 3,995,140.

The present invention pertains to electrically heated windows. It has heretofore been proposed, for example for the rear window of automobiles, to provide resistance heating circuits including a humidity detector comprising electrodes deposited on a surface of the window. These electrodes effect, by means of an amplifier, the energization of electric resistances on the window until the humidity between the electrodes has been dissipated. After a sufficient operating time, the heated portion of the window provides a transparent area of visibility, the size of which is relatively independent of the severity of atmospheric conditions. In these preivously proposed devices, the detector which detects the presence of moisture on the window comprises a system of closely disposed horizontally oriented electrodes located side by side at a small spacing, advantageously in the form of two combs whose teeth are interdigitated. They have been disposed on the inside face of the window, advantageously deposited on the window simultaneously with heating elements which take the form of electrically conductive resistive strips extending horizontally between vertical bus bands. These resistive strips and bus bands, and also the electrodes of the humidity detector and the leads thereto, may comprise finely divided silver suspended with an organic binder in a ceramic frit, the suspension being baked to the glass to produce strips which may optionally be reinforced by means of one or more electroplating operations.

In the presence of humidity on the surface of the window, an electric current can pass between the electrodes of the humidity detector, thereby providing a signal which serves to energize the heating circuit. Experience has however shown that automatic operation of such systems is not entirely satisfactory under some severe conditions, in particular when the thickness of the deposit of humidity is large. Thus it may occur that the heating circuit remains energized even after the area of interest on the window, spanned by the resistive conductors which make up the heating circuit, has been freed of snow, sleet or moisture.

It is an object of the invention to provide an automatically operating electrically heated window including an improved humidity detector which insures dependable operation.

According to one feature of the invention, the conductors which constitute the humidity detecting electrodes are disposed vertically, i.e. substantially in the direction of the maximum slope of the window as assembled into a motor car. It has been found that a principal cause of imperfect operation of the known detectors is that the detector electrodes, being in relief on the surface of the window, increase the tendency of the moisture to collect in drops or droplets whose elimination is difficult. Such a droplet may bridge the space between two electrodes of opposite polarity in the detector and thus impair the operation of the system by maintaining the heating circuit energized longer than is necessary. Roughening the surface which supports the electrodes reduces this adverse effect but does not entirely suppress it. When the electrodes are disposed in accordance with the invention, drops of water (produced either by condensation or agglomeration of moisture such as results from the melting of frost), roll or flow downward, lengthwise of the electrodes of the detector and beyond the lower limit thereof. The motions of the vehicle, including those due to road shocks, promote such a flow of droplets, so that the signal for energization of the heating conductor is not undesirably prolonged. The exact orientation of the conductors of the detector may be selected to take into account air currents such as those due to the motion of the vehicle.

According to a second feature of the invention, and in order to insure effective elimination of droplets, it is preferable that each conductor of one electrode (e.g. of one comb) be extended below the lower end of the conductors of the other electrode at least insofar as they are laterally opposite one another. With this arrangement there is reduced likelihood that a drop bridging the two electrodes may remain attached at lower end thereof because in its downward motion it will more easily detach itself from one electrode (the one which terminates higher on the window) and then from the other. When the two humidity detector electrodes connect to leads at the same height, it is possible to achieve such a construction by causing the two electrodes to extend downwardly from the leads and by giving a greater length to one than to the other. It is however also possible to give the same length to the vertical conductors which constitute the electrodes of the detector, provided they are displaced from each other lengthwise. This will be achieved in part when the electrodes take the shape of combs each including plural teeth connected to a lead, an upper one and a lower one. The vertical teeth of the upper comb electrode may then terminate at their lower ends several millimeters above the connection of the teeth of the lower comb electrode to their lead.

It is of course known that the humidity detector or detectors should be disposed within the area on the window from which the heating conductors are capable of removing moisture by heat.

According to a further feature of the invention, the detector electrodes are disposed at or near the edge of that area, and more particularly with the vertically extending electrodes of the detector according to the invention near a horizontal edge of that area, for example a few millimeters from one of the resistance heating conductors in case of a heater comprising narrow, horizontal resistance conductors fed from vertical bus bands at the sides. In this way there is obtained good operation over a wide range of atmospheric conditions. Lastly, it has been observed that, especially in cold weather, the formation of small droplets may interfere with proper operation. These droplets may be due to re-condensation of humidity on the cold inside surface of the window. They tend to gather, especially when the heater conductors are first energized, along the horizontal leads to the humidity detector electrodes, and then to enter through the force of gravity and also through capillary action into the active zone, i.e. between detector electrodes of opposite polarity.

According to still a further feature of the invention, the lead or leads to the detector electrodes are formed to act as a gutter which ends outside the active zone of the detector. This gutter may take various shapes of which a number will be hereinafter disclosed in exemplary fashion. It is primarily significant to note that the leads to the detector electrodes should be shaped to avoid long horizontal runs since that would result in a large gathering of droplets and result in undesirable flow paths therefor. On the other hand, it is advantageous to design the upper comb in such fashion that it will extend to both sides of the lower comb, thus preventing the formation of undesirable water flow paths and obliging the water to flow to either side of the area occupied by the humidity detector electrodes instead of through it. It is moreover preferable to extend each gutter to the lowest limit of the humidity detector and to the vicinity of the heating conductors so as to insure dissipation from the window, by the heat developed in the heating conductors, of water gathered by such gutters.

BRIEF DESCRIPTION OF THE DRAWINGS

The invention will now be further described in terms of a number of presently preferred exemplary embodiments and by reference to the accompanying drawings in which:

FIG. 1 shows a first form of thermal window in accordance with the invention;

FIG. 2 is a figure similar to that of FIG. 1 but showing a modified form of thermal window according to the invention;

DESCRIPTION OF PREFERRED EMBODIMENTS

Figure 3:
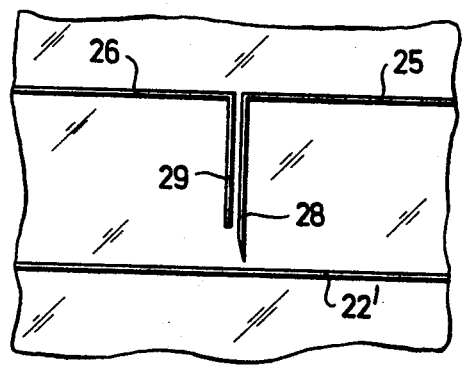
FIG. 3 is a detail view at an enlarged scale of one form of humidity detector similar to that shown in FIG. 1.

The heated window shown in FIG. 1 comprises a single sheet of tempered glass 1, although the invention is not limited to the use of tempered glass.

The heating resistance comprises narrow horizontal resistive, conductive strips 2 produced by the silk screen printing onto the glass of a paste including metal particles and a glass frit, baked to the surface of the glass at high temperature, advantageously in the course of a thermal treatment for tempering and/or for bending of the glass. The conducting strips 2 are fed from lateral bus bands 3 and 4 made of the same material as the strips 2 and laid down at the same time. The strips 2 and bus bands 3 and 4 may be described as forming a heating grid. Connectors for the wires which extend from the bus bands to a switch and to the vehicle battery, though not shown in the figure, are subsequently applied.

Above the top-most heating strip 2' are disposed two leads 5 and 6. Lead 5 connects to the bus band 3 and lead 6 connects to a separate terminal 7 which may be physically adjacent to the bus band 4 but which is electrically distict therefrom. The two leads permit application of a potential difference to the humidity detector which comprises two substantially vertically oriented, closely spaced short conductors or electrodes 8 and 9. The leads 5 and 6 and the electrodes 8 and 9 are made of the same material as the heating strips 2 and are laid down at the same time as those strips and may advantageously possess a similar width and thickness. The strips 2, bus bands 3 and 4, leads 5 and 6, terminal 7 and electrodes 8 and 9 are all formed on the face of the glass which is exposed to the interior of the vehicle.

The electrodes 8 and 9 have the same length, which may be on the order of 2 to 3 centimeters, and their free ends reach nearly but not quite to the upper limit of the top-most heating resistance strip 2'. Their separation may be between 0.2 and 1 mm.

FIG. 2 shows another embodiment of the window of the invention, again including a single sheet of tempered glass 11. The concave face of the glass, to be turned to the interior of the vehicle, bears heating resistances 12 and lateral bus bands 13 and 14 made from a ceramic paste including a conductive material and baked to the surface of the glass. The humidity detector, comprising two electrodes 18 and 19 which take the form of combs interdigitated one into the other, is disposed at one side of the glass in the vicinity of the bus band 13. It has appeared that in most cases, when the window is the rear window of a vehicle, the corners of the area which is to be kept clear by operation of the heating conductors are the last parts of that area to be freed of fog or condensation. By placing the humidity in one of those corner positions, a good clearing of the center portion of the window is assured. The electrodes 18 and 19 are connected to two leads 15 and 16, one connecting to the bus band 13 and the other to a separate terminal 17.

FIG. 3 shows, at full scale, one form of detector similar to that of FIG. 1. This humidity detector is disposed on the glass of the window above the highest heating strip 22' and comprises two vertical electrodes 28 and 29 disposed side by side at a small separation from each other. They are fed at their upper ends by two leads 25 and 26. The electrode 28 is longer by a few millimeters than the electrode 29. Its lower end is advantageously pointed, to facilitate the detachment of water droplets therefrom.

In this construction as in the previously described embodiment of FIG. 2, water droplets which may form between the electrodes 28 and 29 readily separate from the lower end of the shorter electrode 29 and flow downwardly along the extension of the longer electrode 28. The drops of water which flow along this extension to the immediate vicinity of the heating strip 22' evaporate under the influence of the heat evolved by the latter.

Figure 4:
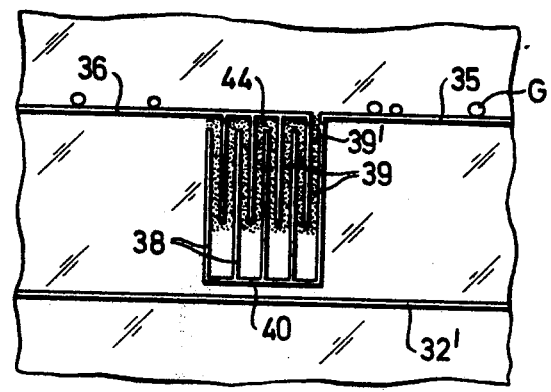
FIG. 4 is a detail view at an enlarged scale of the humidity detector of the window of FIG. 2.

By multiplying the number of electrodes in parallel one obtains one or more humidity detectors such as that illustrated in FIG. 4, which differs from that of FIG. 3 by having a greater sensitivity.

FIG. 4 shows at an enlarged scale the interdigitated comb electrodes 18 and 19 of the humidity detector of FIG. 2. Electrode 18 comprises a collector or lead 40 and a plurality of vertical conductors 38 forming a comb. Electrode 19 comprises a similar collector or lead 44 and a plurality of vertical conductors 39 likewise forming a comb, the teeth 38 of the lower comb 18 being interdigitated with the teeth 39 of the upper comb 19. Comb 19 connects at its lead 44 to a horizontal lead 36 collinear with lead 44. Comb 18 connects via one of its teeth 38 to a horizontal lead 35 collinear with lead 36.

The lead or collector 40 is disposed parallel to the heating resistance strip 32' at a short distance therefrom, for example of the order of 1 mm. Water droplets which form on the humidity detector flow lengthwise of the vertical teeth 39 and then lengthwise of teeth 38 to the lead 40, especially under the influence of the irregular motions of the vehicle. If they remain on lead 40, they will evaporate in view of their nearness to the heating strip 32'. Teeth 38 having a length of from 15 to 30 mm. and teeth 39 having a length of from 10 to 20 mm., with a spacing between adjacent teeth of the two combs of from 0.3 to 0.5 mm. and a similar width for the teeth, have given good results. The active zone of the detector is the area in which the lengths of the teeth 38 and 39 are overlapping, and this area on the glass may be roughened, as indicated by stippling in the figure.

In the humidity detectors hereinabove described, for example in that of FIG. 4, there exists near the adjacent ends of the leads 35 and 36 a channel permitting water droplets G which may collect along the upper edge of those leads to flow through the edge portion of the active zone above described. Thus this channel may be disposed between the right-hand tooth 38 and the right-hand tooth 39.

FIGS. 5 through 8 illustrate further particular advantageous forms of humidity detectors according to the invention.

Figure 5:
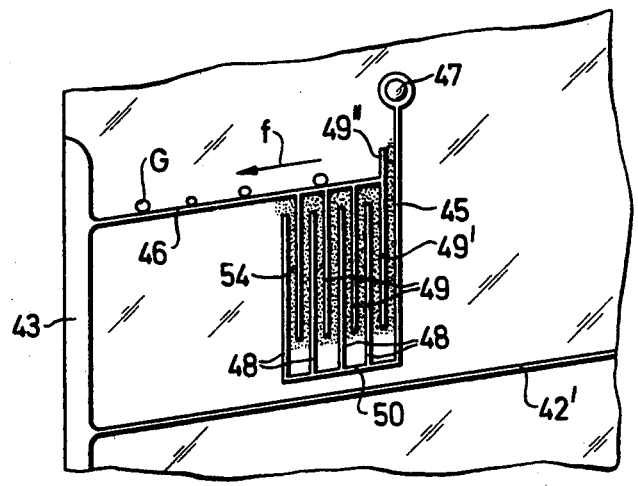
FIGS. 5 to 8 are figures similar to that of FIGS. 3 and 4 but showing variant constructions of the humidity detector in accordance with the invention.

The detector of FIG. 5 is disposed above the highest heating resistance strip 42' and adjacent the bus bar 43 of the heating grid of the heated window fragmentarily shown in that figure. Leads 45 and 46, connecting respectively to a separate terminal 47 and to the bus band 43, feed complementary groups of interdigitated comb teeth-like electrodes 48 and 49. The electrodes 48 are connected to a lower lead 50 disposed in the vicinity of the heating strip 42' and connecting to the lead 45. The latter connects vertically to the terminal 47. The lead which connects electrodes 49 to each other comprises the end of the lead 46. The active zone of the detector is the zone 54 shown stippled in the figure.

A channel is provided through the zone 54 between the right-most electrode 49' and the vertical lead 45 for run-off of water droplets. The lead 46 is however not horizontal and thus forms, on the glass, a gutter to carry other droplets G in the direction of the arrow f away from the active zone 54. These other water droplets may thereafter flow harmlessly and without hindrance lengthwise of the vertical bus band 43. The extreme electrode 49' may be extended as indicated at 49'' to prevent all flow of droplets from the conductor 46 to the interior of the detector, i.e. into the zone 54.

Figure 6:
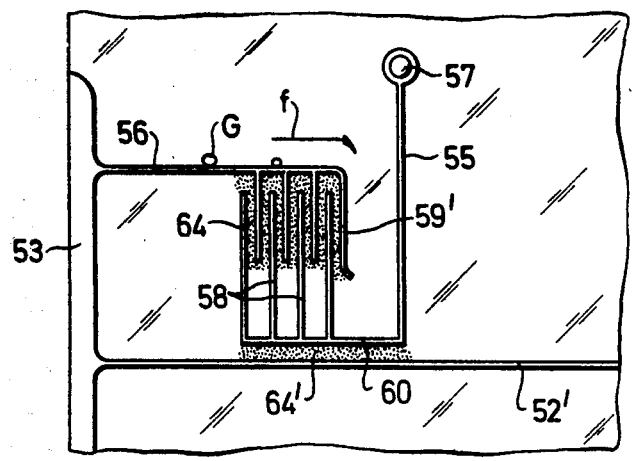

The construction shown in FIG. 6 is similar to that of FIG. 5 but the horizontal lead 56 does not have the inclination of the lead 46 in FIG. 5, and the vertical lead 55 to the electrodes 58 of the lower comb is spaced from the extreme electrode 59' of the upper comb more widely than the spacing of lead 45 from the right-most electrode 49' in FIG. 5. The spacing of lead 55 from electrode 59', which may be from 3 to 5 mm., prevents lead 55 from functioning with electrode 59' as part of the detector. However, the two define a gutter or flow path for water drops, as indicated by the arrow f, from the lead 56 (which may be horizontal, without inclination) down onto the lead 60. Lead 60, at a distance of the order of from 1 to 3 mm. from the heating resistance 52', is close enough to the latter so that droplets held on lead 60 will be evaporated by heat there evolved.

According to the electronic circuit associated with the detector for operation of the switch controlling application of power to the heating conductors and according to the distribution of voltage drops among those conductors, the active zone 64 may be supplemented by a zone 64' in view of the proximity of the two conductors 60 and 52', zone 64' being likewise shown stippled in the figure.

Figure 7:
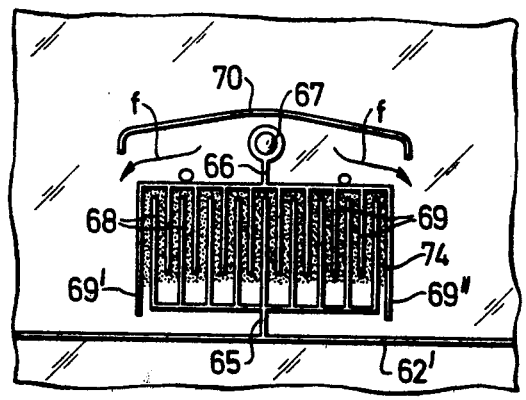

In the embodiment represented in FIG. 7, the humidity detector includes a separate output terminal 67. The current leads 65 and 66 to the two combs are vertical and the conductor 65 is connected directly to the heating strip 62'. The electrodes 69 of the upper comb, with the substantially horizontal lead connecting them to vertical lead 66, and especially with the extreme electrodes 69' and 69'', forms a "roof" covering the entire active zone 74 of the detector and protecting it from water droplets which might otherwise flow down into that zone from locations higher up on the surface of the glass. A further protective gutter may be provided by the provision of a conducting strip 70 above the terminal 67.

Figure 8:
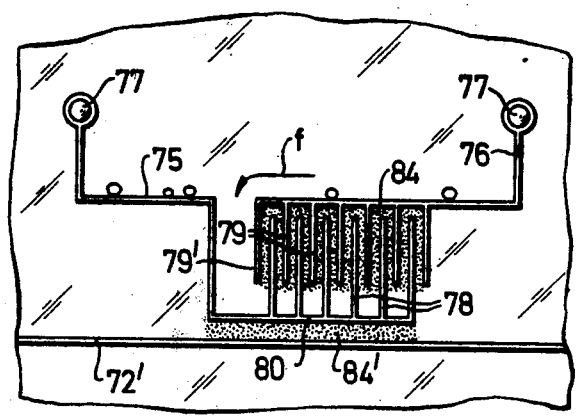

In the embodiment of FIG. 8, the lead 75 to the electrodes 78 of the lower comb includes at the left a vertical extenion, widely spaced however from the electrodes 79 and 78 of the upper and lower combs. Hence water droplets flowing downwardly between that vertical extension and the left-most electrode 79' come to rest on the lower horizontal portion 80 of lead 75 and are there evaporated.

Suitable amplifying circuits for use with the humidity detectors of the invention are disclosed in the copending application Ser. No. 227,074 which is assigned to the assignee hereof and in the continuation-in-part thereof Ser. No. 465,164, filed Apr. 29, 1974, now abandoned.

The invention is of course not limited to the use of single sheets of glass. Laminated glass can be employed, with the heating conductors either on an exterior face thereof as hereinabove described or disposed in the plastic inter-layer between outer glass layers. The invention may also employ transparent sheets on whch the heating resistance takes the form of a transparent coating, for example of tin oxide, or the form of one or more metallic and/or semi-conducting layers. In all embodiments the humidity detector itself is disposed on the face of the window turned to the inside of the vehicle and is preferably baked directly onto the surface of the glass, although it is possible for it to be disposed on a distinct, separate support.

While the invention has been described hereinabove in terms of a number of presently preferred embodiments, the invention is not limited thereto, but rather includes all modifications of and departures from those embodiments properly falling within the scope of the appended claims.

We claim:

1. A thermal window comprising a smooth surfaced transparent sheet which is inclined from the horizontal when installed for use, a plurality of spaced electric resistance heating conductors on the sheet extending generally horizontally, terminal means for connecting said heating conductors in circuit with a source of electrical power, and a humidity detector including at least two conductors closely spaced from each other affixed to and standing in relief from the inside surface of the sheet, said conductors of the humidity detector extending substantially perpendicular to said heating conductors so as to extend in a direction of maximum slope of said sheet when installed for use with one of the conductors extending below the lower terminus of the other of the conductors and closely approaching one of said heating conductors.

2. A thermal window according to claim 1 in which the lower extremity of said one conductor of the humidity detector is pointed.

3. A thermal window according to claim 1 in which said conductors of the humidity detector are positioned above and closely adjacent the uppermost of said heating conductors.

4. A thermal window according to claim 1 including strip means on the inside surface of said sheet above said conductors of said humidity detector and extending thereover, said strip standing in relief from the inside surface to a height sufficient to divert water droplets from the area between said conductors of the humidity detector.

* * * * *